(12) United States Patent
Hammerberg (10) Patent No.: US 11,357,422 B2
(45) Date of Patent: Jun. 14, 2022

(54) GRADATED COMPOSITE MATERIAL FOR IMPACT PROTECTION

(71) Applicant: Alexandra G. Hammerberg, Seattle, WA (US)

(72) Inventor: Alexandra G. Hammerberg, Seattle, WA (US)

( * ) Notice: Subject to any disclaimer, the term of this patent is extended or adjusted under 35 U.S.C. 154(b) by 0 days.

(21) Appl. No.: 16/418,752

(22) Filed: May 21, 2019

(65) Prior Publication Data
US 2019/0328280 A1 Oct. 31, 2019

Related U.S. Application Data

(60) Provisional application No. 62/675,321, filed on May 23, 2018.

(51) Int. Cl.
*A61B 5/103* (2006.01)
*A61B 5/00* (2006.01)
*B32B 5/02* (2006.01)
*B32B 5/18* (2006.01)
*B32B 5/24* (2006.01)
(Continued)

(52) U.S. Cl.
CPC .......... *A61B 5/1036* (2013.01); *A61B 5/0022* (2013.01); *A61B 5/6812* (2013.01); *B32B 5/028* (2013.01); *B32B 5/18* (2013.01); *B32B 5/245* (2013.01); *B32B 5/32* (2013.01); *B32B 7/02* (2013.01); *B32B 27/12* (2013.01); *B32B 27/40* (2013.01); *A61B 2562/0247* (2013.01); *B32B 2262/106* (2013.01); *B32B 2266/0278* (2013.01); *B32B 2305/022* (2013.01);
(Continued)

(58) Field of Classification Search
CPC ........................................................ B32B 3/08
See application file for complete search history.

(56) References Cited

U.S. PATENT DOCUMENTS 4,130,614 A 12/1978 Saidla
5,173,227 A 12/1992 Ewen
(Continued)

FOREIGN PATENT DOCUMENTS

JP 2010178935 A * 8/2010 ............. A47C 27/16
WO 2010059198 5/2010

OTHER PUBLICATIONS

EPO Machine Translation of JP 2010178935 A. Retrieved on Mar. 23, 2020 from https://worldwide.espacenet.com (Year: 2020).*
(Continued)

*Primary Examiner* — Allen Porter
*Assistant Examiner* — Samuel C Kim
(74) *Attorney, Agent, or Firm* — Jesse S Kindra (57) ABSTRACT

A gradated composite material for impact protection is provided. The material includes an inner cushioning layer and an outer shell layer. The material includes a plurality of foam layers, each foam layer having a foam thickness, wherein at least some of the foam layers have differing foam thicknesses. The material includes a plurality of mesh layers, each mesh layer having a mesh porosity, wherein at least some of the mesh layers have differing mesh porosities. The foam layers and the mesh layers are positioned in an alternating arrangement between the inner cushioning layer and the outer shell layer such that each foam layer is adjacent to at least one mesh layer, and each mesh layer is adjacent to at least one foam layer.

17 Claims, 4 Drawing Sheets

(51) Int. Cl.
*B32B 5/32* (2006.01)
*B32B 7/02* (2019.01)
*B32B 27/12* (2006.01)
*B32B 27/40* (2006.01)

(52) U.S. Cl.
CPC ... *B32B 2307/558* (2013.01); *B32B 2307/732* (2013.01); *B32B 2535/00* (2013.01)

(56) References Cited

U.S. PATENT DOCUMENTS

| | | | |
|---|---|---|---|
| 5,389,316 A | 2/1995 | Kerman | |
| 6,063,716 A * | 5/2000 | Granqvist | F41H 5/0485 442/246 |
| 6,070,273 A * | 6/2000 | Sgro | A41D 13/0153 2/455 |
| 6,216,545 B1 | 4/2001 | Taylor | |
| 6,505,421 B1 * | 1/2003 | Vaz | A43B 3/0026 36/25 R |
| 6,823,548 B2 * | 11/2004 | Murphy | A47C 31/001 5/698 |
| 7,393,577 B2 | 7/2008 | Day | |
| 7,726,206 B2 | 6/2010 | Terrafranca | |
| 7,799,710 B1 * | 9/2010 | Tan | B32B 5/22 442/221 |
| 2001/0001687 A1 * | 5/2001 | Pokorzynski | B32B 27/065 428/318.6 |
| 2003/0134103 A1 * | 7/2003 | Novak | B29C 44/1209 428/317.9 |
| 2003/0180517 A1 * | 9/2003 | Karall | A43B 13/38 428/304.4 |
| 2008/0086916 A1 * | 4/2008 | Ellis | A43B 13/141 36/103 |
| 2009/0047453 A1 | 2/2009 | Folaron | |
| 2010/0143661 A1 * | 6/2010 | Warrick | F16F 1/40 428/174 |
| 2010/0324455 A1 * | 12/2010 | Rangel | A43B 3/0005 600/592 |
| 2012/0066838 A1 * | 3/2012 | Smalling | A47C 23/005 5/718 |
| 2012/0084896 A1 * | 4/2012 | Wyner | B32B 27/30 2/16 |
| 2012/0291564 A1 | 11/2012 | Amos | |
| 2013/0303041 A1 * | 11/2013 | Kim | B32B 27/40 442/1 |
| 2015/0279345 A1 | 10/2015 | Mathur | |
| 2016/0015311 A1 * | 1/2016 | Jiang | A61B 5/6892 623/33 |
| 2016/0221303 A1 * | 8/2016 | Jancar | B32B 5/245 |
| 2016/0302507 A1 * | 10/2016 | Lewis | F41H 1/08 |
| 2017/0059426 A1 * | 3/2017 | Choi | G01L 5/00 |
| 2018/0311929 A1 * | 11/2018 | Mason | B32B 19/045 |

OTHER PUBLICATIONS

SurroSense Rx, http://www.academymedical.net/wp-content/uploads/2016/05/Orpyx-SurroSense-Rx-Academy-Medical-Brochure-160503.pdf, Orpyx Medical Technologies Inc. (accessed Mar. 1, 2018).
Fu, M. et al., Haptic Biofeedback for Improving Compliance With Lower-Extremity Partial Weight Bearing, Orthopedics, Nov. 2014.
Overview: In-Shoe Pressure Measurement Technology, https://www.tekscan.com/print/product-group/medical/in-shoe, Tekscan (accessed Mar. 1, 2018).
https://www.rockwestcomposites.com/samples-fabrics (accessed May 14, 2019).

* cited by examiner

GRADATED COMPOSITE MATERIAL FOR IMPACT PROTECTION

CROSS-REFERENCE TO RELATED APPLICATION

The present application claims the benefit of U.S. Provisional Application No. 62/675,321, filed May 23, 2018, which is incorporated by reference herein in its entirety.

BACKGROUND

Wearable protective devices such as footwear, headgear, and body armor are used in a wide variety of sports, military, industrial, and medical applications to protect against injury. However, existing materials utilized in wearable protective devices may exhibit significant shortcomings. For example, soft materials used to provide cushioning and shock absorption can be easily torn and deformed, while hard materials used to provide strength and puncture resistance can be brittle and uncomfortable to wear. Additionally, existing materials often lack any functionality for detecting impacts on the wearer's body, which may hinder the wearer's ability to avoid injury or determine whether to seek medical treatment. Thus, there is a need for new materials that include provide impact protection, wearer comfort, and better feedback regarding absorbed impacts.

DETAILED DESCRIPTION

A multi-layer gradated composite material for impact protection and sensing is described herein. The composite material includes alternating layers of a soft foam material (e.g., polyurethane foam) and a hard mesh material (e.g., carbon fiber mesh). The alternating foam and mesh layers are positioned between an inner cushioning layer (e.g., a polyurethane foam layer), which serves as a soft cushioned interface against the wearer's body, and an outer shell layer (e.g., a carbon fiber shell), which serves as a hard protective surface. The properties of the foam layers and/or mesh layers are gradated to provide a gradual transition of material properties from the soft inner cushioning layer to the hard outer shell layer. For example, the thicknesses of the foam layers may be gradated, such that foam layers closer to the inner cushioning layer have greater thicknesses than foam layers farther from the inner cushioning layer. Alternatively or in combination, the porosities of the mesh layers may be gradated, such that mesh layers located closer to the inner cushioning layer have higher porosities than mesh layers located farther from the inner cushioning layer. The combination of soft foam layers and hard mesh layers with gradated properties results in a mechanically tough material capable of dissipating impact energy while maintaining wearer comfort.

In some embodiments, the gradated composite material includes at least one embedded pressure sensor (e.g., a piezoresistive pressure sensor) configured to detect applied pressures and/or forces. The pressure and/or force data may be transmitted to an external device (e.g., a mobile device or computer) for collection, monitoring, and/or feedback.

The gradated composite material described herein may be incorporated into protective footwear, headgear, body armor, and other types of wearable devices designed to protect the wearer's body against injury. For example, an orthopedic device for protecting a patient's foot is described herein. The orthopedic device includes a foot-receiving portion incorporating the gradated composite material, and at least one pressure sensor configured to detect pressures and/or forces on the patient's foot. The foot-receiving portion is constructed with a gradated composite material, the gradated composite material comprising: a plurality of foam layers, each foam layer having a foam thickness, wherein at least some of the foam layers have differing foam thicknesses; and a plurality of mesh layers, each mesh layer having a mesh porosity, wherein at least some of the mesh layers have differing mesh porosities, wherein the foam layers and the mesh layers are positioned in an alternating arrangement such that each foam layer is adjacent to at least one mesh layer, and each mesh layer is adjacent to at least one foam layer. The orthopedic device may include a transmitter located on or within the foot-receiving portion and configured to transmit the pressure and/or force data to an external device. The external device may be configured to generate a notification in response to the received data, such as an alert notifying the patient that the pressure on the foot exceeds a threshold level. Thus, the orthopedic device protects the patient's foot from injury while providing real-time monitoring and feedback to facilitate the recovery process.

It will be appreciated that the composite material structure described herein may be utilized in other applications in which the impact-absorbing capabilities of the material are not relied upon. For example, the material may be used in applications in which the structural strength and lightweight nature of the material are important, but the application does not anticipate the occurrence of impact to the material during use.

Various embodiments of the technology will now be described. The following description provides specific details for a thorough understanding and an enabling description of these embodiments. One skilled in the art will understand, however, that the technology may be practiced without many of these details. Additionally, some well-known structures or features may not be shown or described in detail, so as to avoid unnecessarily obscuring the relevant description of the various embodiments. The terminology used in the description presented below is intended to be interpreted in its broadest reasonable manner, even though it is being used in conjunction with a detailed description of certain specific embodiments of the technology.

Figure 1:
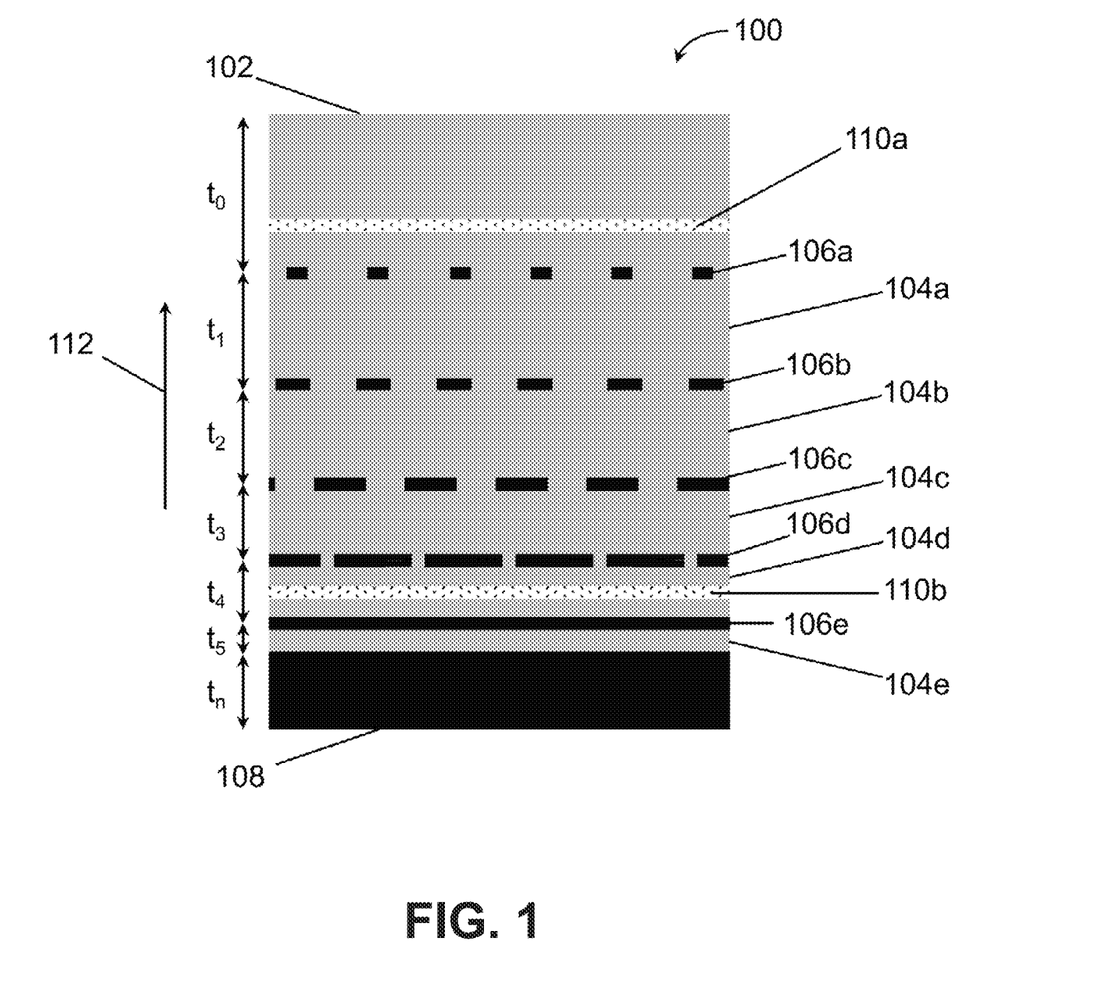
FIG. 1 is a cross-sectional diagram of a multi-layer gradated composite material.
Figure 2:
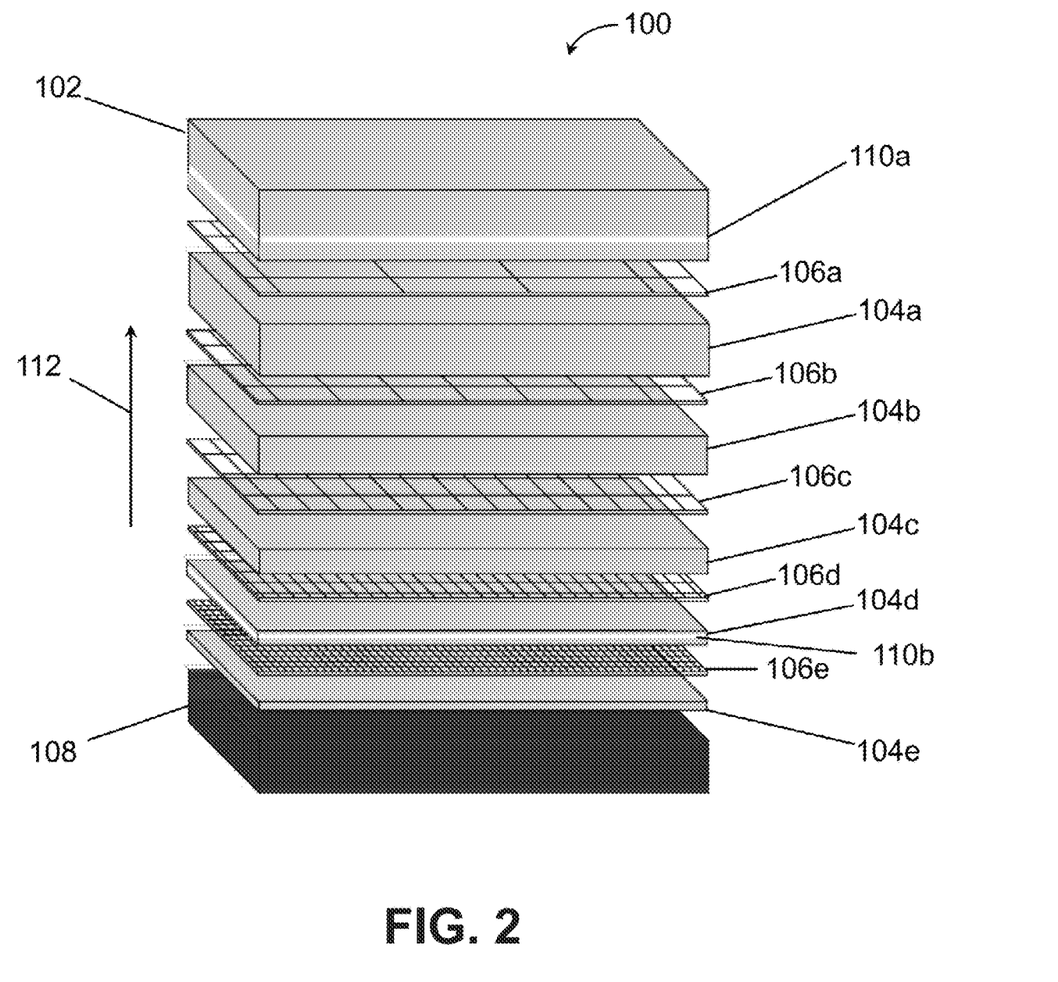
FIG. 2 is an exploded view showing the different layers of the multi-layer gradated composite material of FIG. 1.

FIGS. 1 and 2 illustrate a multi-layer gradated composite material 100. FIG. 1 is a cross-sectional diagram of the composite material 100, and FIG. 2 is an exploded view showing the different layers of the composite material 100. The material 100 includes an inner cushioning layer 102, a plurality of foam layers 104a-e, a plurality of mesh layers 106a-e, and an outer shell layer 108. The foam layers 104a-e and mesh layers 106a-e are positioned between the inner cushioning layer 102 and outer shell layer 108 in an alternating arrangement, such that each of the foam layers 104a-e is adjacent to at least one of the mesh layers 106a-e, and each of the mesh layers 106a-e is adjacent to at least one of the foam layers 104a-e.

The inner cushioning layer 102 serves as an interface between the wearer's body and the remaining portions of the material 100. Thus, the inner cushioning layer 102 may be made of a relatively soft and elastic material that provides cushioning and is comfortable when placed against the body. In some embodiments, the inner cushioning layer 102 is made of memory foam, such as polyurethane foam (e.g., flexible polyurethane foam (FPF)). The inner cushioning layer 102 may include or be covered with a fabric layer, such as a wickable fabric, that is in contact with the wearer's skin. The wickable fabric is selected for wearer comfort, with the intent to prevent rubbing or chafing as well as to minimize the amount of moisture maintained in contact with the wearer's skin. The inner cushioning layer 102 and/or fabric layer may have temperature-regulating properties so as to maintain a comfortable temperature and avoid overheating while in contact with the wearer's skin. Additionally, the inner cushioning layer 102 and/or fabric layer may have antibacterial properties to prevent the growth of bacteria during wear. The thickness to of the inner cushioning layer 102 may be within a range from 2 mm to 5 mm.

The stiffness of a material may be described by Young's modulus. In some embodiments, the inner cushioning layer 102 may be made of material having a Young's modulus of less than 1 GPa. In some embodiments, the inner cushioning layer 102 may be made of material having a Young's modulus of between 0-0.8 GPa.

The outer shell layer 108 serves as a protective exterior surface against impacts. Thus, the outer shell layer 108 may be made of a relatively hard and stiff material that provides mechanical strength and toughness, such as a solid carbon fiber shell. The thickness to of the outer shell layer 108 may be within a range from 1 mm to 5 mm.

In some embodiments, the outer shell layer 108 may be made of material having a Young's modulus of less than 1000 GPa, or less than 500 GPa, or less than 300 GPa, or less than 200 GPa, or less than 100 GPa, or a value between 0.8-100 GPa, inclusive.

The foam layers 104a-e are configured to provide shock absorption and dissipation of impact energies. Thus, the foam layers 104a-e may each be made of a relatively soft and elastic material, such as memory foam. For example, the foam layers 104a-e may each be made of polyurethane foam (e.g., FPF). In some embodiments, the foam layers 104a-e are all made of the same material. Alternatively, some or all of the foam layers 104a-e may be made of different materials. The foam layers 104a-e may be made of the same material as the inner cushioning layer 102, or may be made of a different material.

Each of the foam layers 104a-e has a respective foam thickness. For example, in the embodiment depicted in FIG. 1, foam layer 104a has a thickness $t_1$, foam layer 104b has a thickness $t_2$, foam layer 104c has a thickness $t_3$, foam layer 104d has a thickness $t_4$, and foam layer 104e has a thickness $t_5$. The thicknesses of the foam layers 104a-e may be varied as desired. For example, the thickness of each foam layer may be within a range from 1 mm to 5 mm. In some embodiments, at least some or all of the foam layers 104a-e have differing thicknesses. For instance, in FIG. 1, each of the foam layers 104a-e has a different thickness. Alternatively, some or all of the foam layers 104ae may have the same thickness.

The thicknesses of the foam layers 104a-e may be gradated, such that the foam layers 104a-e exhibit variable thicknesses (e.g., increasing or decreasing thicknesses) along the direction 112 from the outer shell layer 108 to the inner cushioning layer 102. For example, in FIG. 1, the foam layers 104a-e exhibit increasing thicknesses along direction 112 (e.g., $t_1 > t_2 > t_3 > t_4 > t_5$), such that foam layers closer to the inner cushioning layer 102 have greater foam thicknesses than foam layers farther from the inner cushioning layer 102, and foam layers closer to the outer shell layer 108 have smaller foam thicknesses than foam layers farther from the outer shell layer 108. The thickness to of the inner cushioning layer 102 may be greater than the respective thicknesses of each of the foam layers 104a-e. One advantage of gradated thicknesses of foam layers is that the composite material 100 more effectively absorbs shocks and dissipates impact energies.

Optionally, some of the foam layers 104a-e may have the same thickness (e.g., $t_1 \geq t_2 \geq t_3 \geq t_4 \geq t_5$), such that at least one foam layer near the inner cushioning layer 102 has a greater foam thickness than at least one foam layer away from the inner cushioning layer 102, and at least one foam layer near the outer shell layer 108 has a smaller foam thickness than at least one foam layer away from the outer shell layer 108.

In some embodiments, the foam layers 104a-e may be made of material having a Young's modulus of less than 1 GPa. In some embodiments, the foam layers 104a-e may be made of material having a Young's modulus of between 0-0.8 GPa.

The mesh layers 106a-e are configured to provide strength and toughness. Thus, the mesh layers 106a-e may each be made of a relatively hard and stiff material, such as a carbon fiber mesh made of cross-woven fibers. The mesh may include long bundles of aligned fibers that are woven together for improved strength. Alternatively, the fiber bundles may be interconnected in a cross-hatched pattern or other pattern without weaving (e.g., using chemical, mechanical, or heat bonding). The mesh may be impregnated with a resin (e.g., a "prepreg" mesh), or may be provided without resin. In some embodiments, the mesh layers 106a-e are all constructed using the same technique (e.g., weaving). Alternatively, some or all of the mesh layers 106a-e may be constructed using different techniques (e.g., some layers may be woven and some layers bonded). Alternatively, some or all of the mesh layers 106a-e may be constructed by deconstructing pre-woven material. For example, pre-woven material may be deconstructed by removal of fiber bundles to create meshes of different porosities.

In some embodiments, the mesh layers 106a-e are all made of the same material. Alternatively, some or all of the mesh layers 106a-e may be made of different materials. The mesh layers 106a-e may be made of the same material as the outer shell layer 108, or may be made of different materials. In some embodiments, the mesh layers may be made of carbon fiber. In some embodiments, the mesh layers may be made of woven carbon fiber. In some embodiments, the mesh layers may be made of plain weave dry carbon fiber fabric. In some embodiments, the mesh layers may be made of plain weave dry carbon fiber fabric that has been altered to create different porosities.

In some embodiments, the mesh layers 106a-e may be made of material having a Young's modulus of less than 200 GPa. In some embodiments, the mesh layers 106a-e may be made of material having a Young's modulus between 0.8-200 GPa.

As can be seen in FIG. 2, each of the mesh layers 106a-e has a respective mesh porosity. The mesh porosity may be inversely correlated to the tightness and density of the mesh weave, and directly correlated with the size of the mesh openings, such that meshes with higher porosities have looser weaves and larger openings, and meshes with lower porosities have tighter weaves and smaller openings.

In the embodiment depicted in FIG. 2, mesh layer 106a has a porosity $p_1$, mesh layer 106b has a porosity $p_2$, mesh layer 106c has a porosity $p_3$, mesh layer 106d has a porosity $p_4$, and mesh layer 106e has a porosity $p_5$. The porosities of the mesh layers 106a-e may be varied as desired. In some embodiments, at least some or all of the mesh layers 106a-e have differing porosities. For instance, in FIG. 2, each of the mesh layers 106a-e has a different porosity. Alternatively, some or all of the mesh layers 106a-e may have the same mesh porosity.

The porosities of the mesh layers 106a-e may be gradated, such that the mesh layers 106a-e exhibit variable porosities (e.g., increasing or decreasing porosities) along the direction 112. For example, in FIG. 2, the mesh layers 106a-e exhibit increasing porosities along direction 112 (e.g., $p_1 > p_2 > p_3 > p_4 > p_5$), such that mesh layers closer to the inner cushioning layer 102 have higher mesh porosities than mesh layers farther from the inner cushioning layer 102, and mesh layers closer to the outer shell layer 108 have lower mesh porosities than mesh layers farther from the outer shell layer 108. One advantage of gradated porosities of mesh layers is that the composite material 100 exhibits improved strength and toughness in regions designed to protect from impact (e.g., the outer shell layer) while at the same time providing greater flexibility and comfort in regions designed to be brought into contact with the wearer's body (e.g., the inner cushioning layer).

Optionally, some of the mesh layers 106a-e may have the same porosity (e.g., $p_1 \geq p_2 \geq p_3 \geq p_4 \geq p_5$), such that at least one mesh layer near the inner cushioning layer 102 has a higher mesh porosity than at least one mesh layer away from the inner cushioning layer 102, and at least one mesh layer near the outer shell layer 108 has a lower mesh porosity than at least one mesh layer away from the outer shell layer 108.

Each of the mesh layers 106a-e has a respective thickness. For example, the thickness of each mesh layer may be approximately 1 mm.

The material 100 may include at least one pressure sensor configured to detect pressures and/or forces applied to the material 100. For example, the configuration depicted in FIGS. 1 and 2 includes pressure sensor 110a embedded in the inner cushioning layer 102 and pressure sensor 110b embedded in the foam layer 104d. Some embodiments may include pressure sensors 110a and 110b in other configurations, such as in the same cushioning or foam layer. Various types of pressure sensors may be used, such as piezoresistive pressure sensors. In some embodiments, the pressure sensor includes one or more layers of a piezoresistive material, such as a piezoresistive sheet or mesh. The piezoresistive material may include a metallic mesh printed on a flexible substrate, such that the resistance of the mesh varies when the substrate is placed under tension or compression. The pressure sensor may be a commercially available sensor, such as a force and/or pressure sensing mesh or system manufactured by Tekscan of South Boston, Mass. (e.g., F-Scan in-shoe foot pressure measurement system, I-Scan tactile pressure mapping system, or FlexiForce force sensor).

The pressure sensor may be configured to detect normal forces (e.g., forces parallel to direction 112), shear forces (e.g., forces orthogonal to direction 112), or combinations thereof. In some embodiments, the material 100 includes at least two layers of pressure sensors (e.g., as depicted in FIGS. 1 and 2) to allow for detection of both normal and shear forces.

The pressure sensor may be positioned at various locations relative to the material 100. For example, the pressure sensor may be embedded within the interior of the material 100, such as within one of the foam layers 104a-e or the inner cushioning layer 102. Alternatively, the pressure sensor may be positioned on a surface of the material 100, such as on an inner surface (e.g., on an inner surface of the inner cushioning layer 102) or on an outer surface (e.g., on an outer surface of the outer shell layer 108). In some embodiments, the pressure sensor is permanently affixed to and integrated with the material 100, such that the pressure sensor cannot be removed without destroying the material 100. In alternative embodiments, the pressure sensor may be removably coupled to the material 100.

In embodiments where the material 100 includes multiple pressure sensors, the sensors may each be positioned at a different location in the material 100. For example, the sensors may be positioned in different foam layers (e.g., foam layers 104a-e or inner cushioning layer 102), at different depths within a single foam layer (e.g., as depicted in FIGS. 1 and 2 in which the sensors are positioned at different depths within inner cushioning layer 102), at different overlapping or non-overlapping portions within the horizontal plane of a single foam layer, or combinations thereof. Accordingly, multiple pressure sensors may be used to detect pressures and/or forces applied to different portions of the material 100.

The material 100 may include one or more functional components to facilitate collection, storage, and transmission of pressure and/or force data generated by the pressure sensor. For example, the material 100 may include a transmitter (e.g., a wireless transmitter) configured to transmit data generated by the pressure sensor to an external device (e.g., a mobile device or other computing device). The material 100 may also include a receiver (e.g., a wireless receiver) configured to receive data from an external device, such as instructions for controlling the operation of the pressure sensor, transmitter, or other component. Additional functional components that may be associated with protective footwear, headgear, body armor, and other types of wearable devices built using the material 100 include a processor, non-transitory memory, and/or battery. The functional components may be positioned at various locations on or within the material 100. The functional components may be permanently affixed to and integrated with the material 100, or may be removably coupled to the material 100.

The total thickness of the material 100 (e.g., $t_0 + t_1 + t_2 + t_3 + t_4 + t_5 + t_n$) may be varied as desired. In some embodiments, the total thickness of the material 100 is within a range from 1 cm to 5 cm.

The gradated composite material 100 may be fabricated in various ways. In some embodiments, the material 100 is fabricated by flowing or extruding uncured foam through some or all of the mesh layers 106a-e, then fixing or curing the foam to form some or all of the foam layers 104a-e. Accordingly, in the resultant material 100, at least some of the mesh layers 106a-e include foam (e.g., polyurethane foam) interpenetrated through and flowed or extruded through the mesh (e.g., carbon fiber mesh), thus providing improved interlayer bonding and strength. Other components of the material 100, such as the pressure sensor, may be incorporated into the material 100 by placing the component into uncured foam, then fixing or curing the foam to embed the component in the desired location within the foam. Alternatively or in combination, other techniques may be used to fabricate the material 100, such as lamination.

Although FIGS. 1 and 2 depict an exemplary embodiment of the gradated composite material 100, alternative configurations of the material 100 are also possible. For example, although the embodiment of FIGS. 1 and 2 includes five foam layers 104a-e and five mesh layers 106a-e, the number of foam layers and mesh layers may be varied as desired. Alternative embodiments may include at least two, at least three, at least four, at least five, at least six, at least seven, at least eight, at least nine, or at least ten foam layers; and may include at least two, at least three, at least four, at least five, at least six, at least seven, at least eight, at least nine, or at least ten mesh layers. The number of pressure sensors may also be varied. For example, alternative embodiments may include at least one, at least two, at least three, at least four, at least five, at least six, at least seven, at least eight, at least nine, or at least ten pressure sensors. Additionally, the inner cushioning layer 102, outer shell layer 108, or both, may be omitted.

The gradated composite material described herein may be incorporated in various types of wearable protective devices, including but not limited to footwear (e.g., shoes, boots, insoles), headgear (e.g., hats, helmets, masks), and body armor (e.g., vests, coats, suits, shin guards, elbow pads, knee pads). Accordingly, the material may be used to enhance the protective functions of the wearable device while also providing integrated pressure-sensing capabilities, thus obviating the need for separate sensors to monitor impacts on the wearer's body. Although the following exemplary embodiment is described in terms of orthopedic footwear, one skilled in the art will appreciate that the disclosed technology may also be applied to other types of wearable protective devices.

Figure 3:
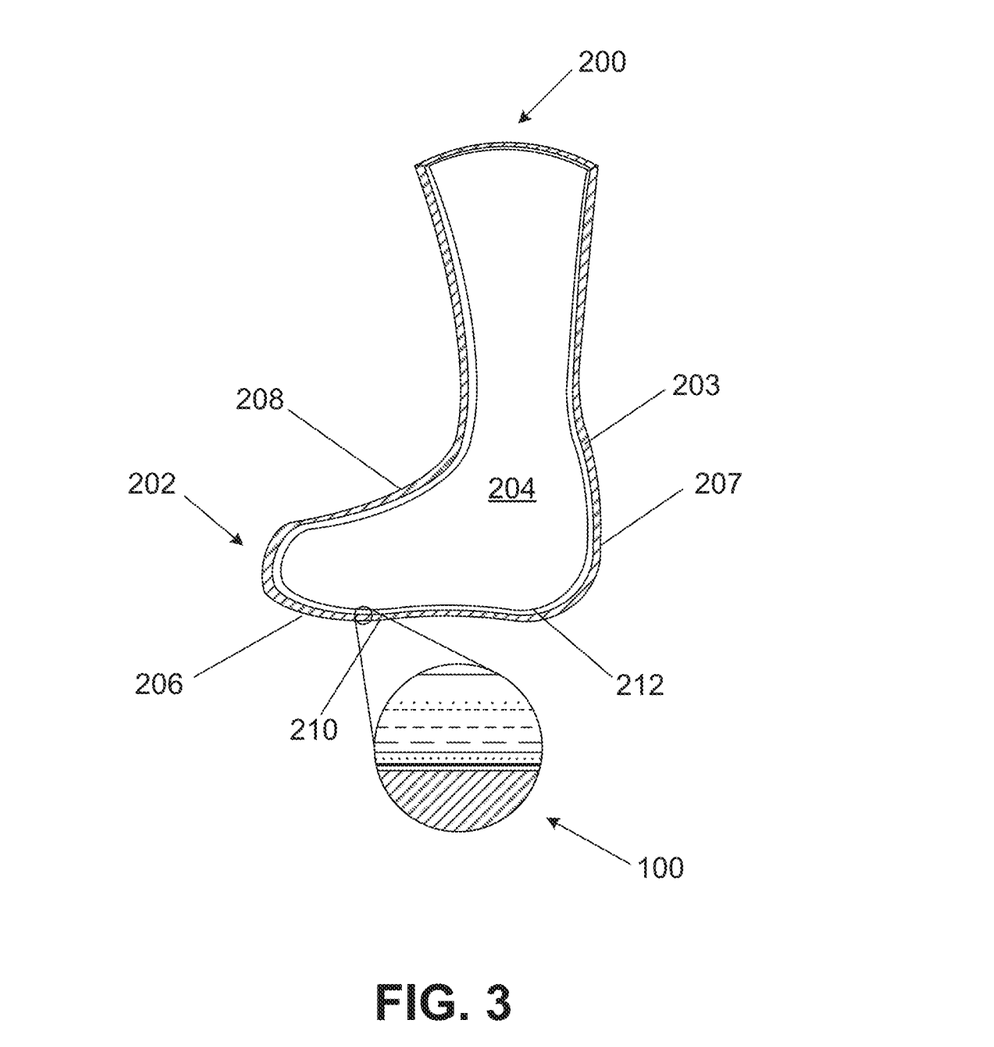
FIG. 3 is a cross-sectional diagram of an exemplary orthopedic device incorporating the multi-layer gradated composite material of FIG. 1.

FIG. 3 is a cross-sectional diagram of an exemplary orthopedic device 200 incorporating the multi-layer gradated composite material 100 of FIG. 1. The device 200 may be a surgical recovery boot, walking boot, brace, or other footwear used to protect a patient's foot after injury or a medical procedure. The device 200 includes a foot-receiving portion 202 having an interior cavity 204 shaped to receive at least a portion of the patient's foot and, optionally, lower leg. The foot-receiving portion includes a sole portion 206, a heel portion 207, and an upper portion 208. When the patient's foot is placed within the cavity 204, the sole portion 206 is positioned near the sole of the foot, the heel portion 207 is positioned near the heel of the foot, and the upper portion 208 is positioned near the upper part of the foot and, optionally, the lower leg.

To allow the device 200 to be placed around the patient's foot, a portion of the upper portion 208 extending down the shin of the patient and partially over the top of the foot may be removable. The removable portion may be hinged (not shown) to the base of the device 200 to allow the removable portion to pivot outward to accommodate the patient's foot (similar to the operation, for example, of a ski boot). Alternatively, the removable portion may be completely detached from the base to facilitate entry of the foot. When the removable portion is returned to its original position, either by pivoting or replacement, the removable portion may be secured to the base of the device 200 via Velcro straps or other securing mechanism. The Velcro straps may extend across the removable portion and around the base of the device to apply pressure and secure the patient's lower leg and/or foot therebetween. The level of pressure may be varied by adjusting the tension on the straps. The device 200 or portions thereof constructed of gradated composite material may be crafted to fit a patient's foot. For example, a 3D structure may be created incorporating mesh layers, and foam may be flowed through the structure such that a gradated composite material as described herein may be crafted to fit a patient's foot. In some embodiments, the device 200 or portions thereof constructed of gradated composite material may be thermally fit to a patient's foot using a 3D structure as described above.

The foot-receiving portion 202 includes the gradated composite material 100 previously described with respect to FIGS. 1 and 2. In the embodiment depicted in FIG. 3, the gradated composite material 100 forms the wall 203 of the foot-receiving portion 202 and extends through the entirety of the foot-receiving portion 202. In alternative embodiments, the gradated composite material 100 may be located only in the sole portion 206, only in the heel portion 207, or only in the upper portion 208.

The alternating foam layers 104a-e and mesh layers 106a-e of the material 100 are positioned between the outer surface 210 and inner surface 212 of the foot-receiving portion 202 to provide impact protection for the patient's foot and/or lower leg. In FIG. 3, the outer shell layer 108 of the material 100 provides the outer surface 210 of the foot-receiving portion 202 and is located away from the patient's foot; the inner cushioning layer 102 of the material 100 provides the inner surface 212 of the foot-receiving portion 202 and is located near the patient's foot. In alternative embodiments, the foot-receiving portion 202 may include other materials on the outer surface 210 and/or inner surface 212, such that the material 100 does not come into direct contact with the exterior environment and/or the patient's foot, respectively.

In some embodiments, the foot-receiving portion 202 includes at least one pressure sensor configured to detect pressures and/or forces (e.g., normal and/or shear forces) on the patient's foot. For example, the pressure sensor may be configured to detect a ground reaction force exerted on the patient's foot while the patient is standing, walking, running, etc. The foot-receiving portion 202 may also include one or more functional components to facilitate collection, storage, and transmission of pressure and/or force data generated by the pressure sensor, such as a transmitter, receiver, processor, non-transitory memory, and/or battery. The pressure sensor and functional components may be located on or within the foot-receiving portion 202. In some embodiments, some or all of these components are incorporated in material 100, as previously described with respect to FIGS. 1 and 2.

Figure 4:
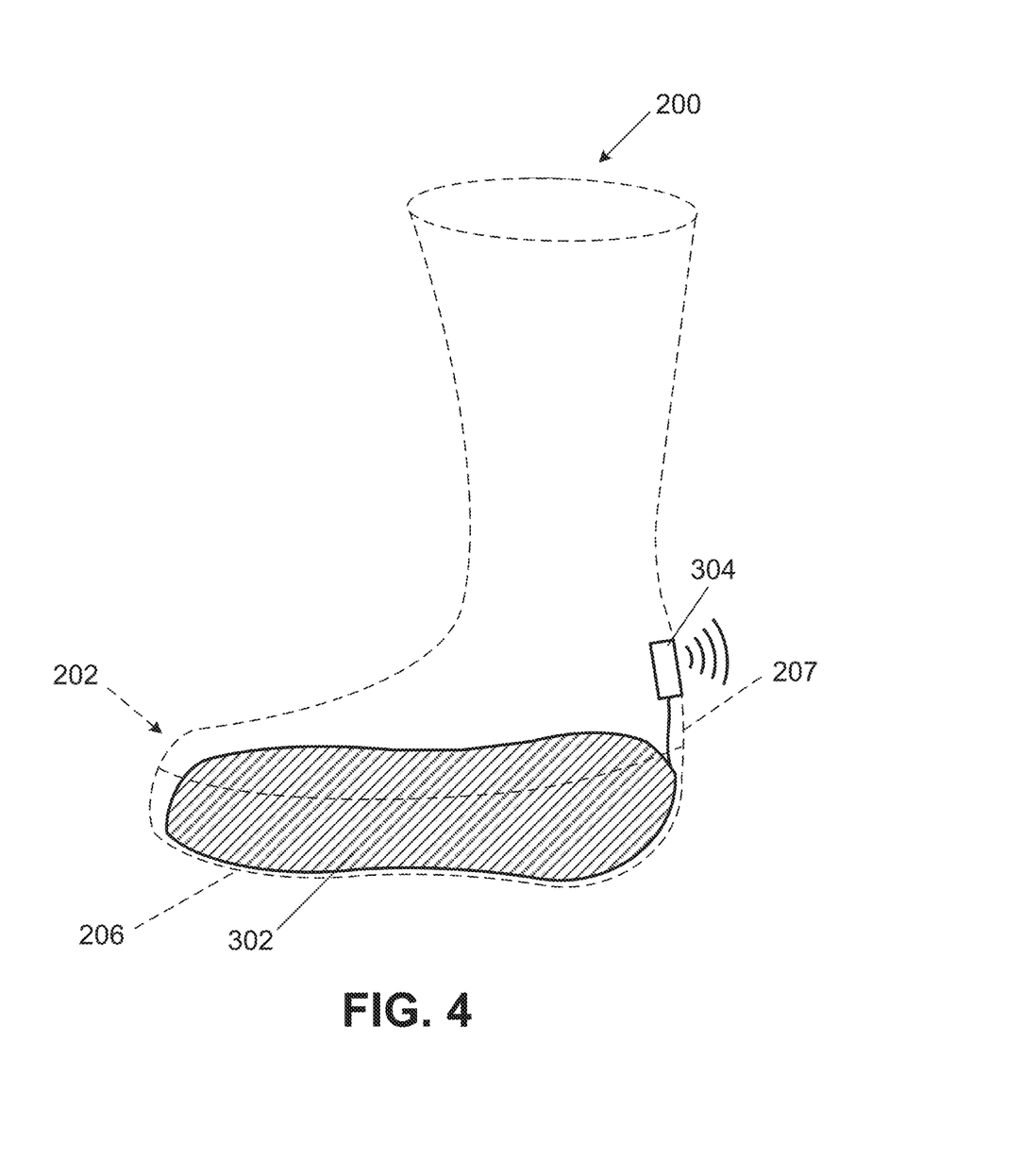
FIG. 4 illustrates an exemplary configuration for a pressure sensor and transmitter within the orthopedic device of FIG. 3.

FIG. 4 illustrates an exemplary configuration for a pressure sensor 302 and wireless transmitter 304 within the orthopedic device 200 of FIG. 3. The pressure sensor 302 is located at the sole portion 206 of the foot-receiving portion 202 so as to detect pressures and/or forces applied to the sole of the patient's foot. For example, the pressure sensor 302 may be used to detect the amount of weight the patient is placing on the foot. The characteristics and function of the pressure sensor 302 may be similar to the pressure sensor previously described with respect to FIGS. 1 and 2. While FIG. 4 depicts the pressure sensor 302 as extending over the entirety of the sole portion 206, it will be appreciated that the pressure sensor may extend for only a portion of the sole portion 206. For example, a smaller pressure sensor may be positioned under the ball of the patient's foot or under the heel of the patient's foot. As another example, rather than a single sensor that extends over the entirety of the sole portion 206, multiple sensors may be positioned at different locations in the sole portion 206 to measure pressure and/or force data at those locations.

The wireless transmitter 304 is located at the heel portion 207 of the foot-receiving portion 202 so as to reduce interference with the patient's foot while the patient is wearing the device 200. The transmitter 304 is configured to transmit pressure and/or force data generated by the pressure sensor to an external device. The characteristics and function of the transmitter 304 may be similar to the transmitter described above with respect to FIGS. 1 and 2.

In some embodiments, the transmitter 304 is configured to transmit data generated by the pressure sensor 302 to an external device configured with software for data collection, patient monitoring, and/or feedback. For example, the data can be transmitted to a computing device associated with the patient wearing the device 200, a computing device associated with the physician treating the patient, a remote server, or a combination thereof. The data may be used by the physician to monitor recovery progress and patient compliance.

In some embodiments, the external device is configured to generate notifications in response to the data. For instance, if the data indicates that the pressures and/or forces on the patient's foot and/or leg exceed a particular threshold specified by the physician (e.g., greater than a certain percentage of the patient's body weight), the external device may alert the patient and/or physician. The alert may help the patient avoid further injury to the foot by providing real-time feedback when acceptable pressure and/or force limits are exceeded.

Although FIGS. 3 and 4 illustrate exemplary embodiments of the orthopedic device 200, one skilled in the art will appreciate that alternative configurations of the orthopedic device 200 are also possible. For example, although the device 200 is depicted as a largely contiguous boot that covers the entirety of the foot and a portion of the lower leg, the size and shape of the device 200 may be varied in alternative embodiments to cover only certain portions of the foot and/or leg.

Additionally, the pressure sensor 302 and/or transmitter 304 may be positioned at other locations on or within the foot-receiving portion 202. For example, the pressure sensor 302 and/or transmitter 304 may be embedded within the wall 203 of the foot-receiving portion 202, or may be attached to the outer surface 210 or inner surface 212. In some embodiments, the pressure sensor 302 includes a layer of material (e.g., piezoresistive sheet or mesh) extending through the entirety of the foot-receiving portion 202, such that pressure and/or force measurements may be obtained across multiple portions of the patient's foot and/or leg. Alternatively, the pressure sensor 302 may be located only at or within certain locations of the foot-receiving portion 202, such as only the sole portion 206, only the heel portion 207, or only the upper portion 208. The transmitter 304 may be located in any portion of the foot-receiving portion 202 that avoids interference with the patient's foot while allowing for wireless signal transmission, such as the sole portion 206, heel portion 207, or upper portion 208.

Although FIG. 4 illustrates a single pressure sensor 302, in alternative embodiments, the device 200 may include a plurality of pressure sensors positioned at multiple different locations on or within the foot-receiving portion 202 to provide pressure and/or force measurements at different portions of the patient's foot and/or leg. In some embodiments, the device 200 may include at least one, at least two, at least three, at least four, at least five, at least six, at least seven, at least eight, at least nine, at least ten, or at least twenty pressure sensors. The data generated by each of the pressure sensors may be transmitted to an external device for data collection, patient monitoring, and/or feedback, as previously described herein.

CONCLUSION

The above Detailed Description of examples of the disclosed technology is not intended to be exhaustive or to limit the disclosed technology to the precise form disclosed above. While specific examples for the disclosed technology are described above for illustrative purposes, various equivalent modifications are possible within the scope of the disclosed technology, as those skilled in the relevant art will recognize. Any specific numbers noted herein are only examples: alternative implementations may employ differing values or ranges.

These and other changes can be made to the disclosed technology in light of the above Detailed Description. While the above description describes certain examples of the disclosed technology, and describes the best mode contemplated, no matter how detailed the above appears in text, the disclosed technology can be practiced in many ways. Details of the device may vary considerably in its specific implementation, while still being encompassed by the technology disclosed herein. As noted above, particular terminology used when describing certain features or aspects of the disclosed technology should not be taken to imply that the terminology is being redefined herein to be restricted to any specific characteristics, features, or aspects of the disclosed technology with which that terminology is associated. In general, the terms used in the following claims should not be construed to limit the disclosed technology to the specific examples disclosed in the specification, unless the above Detailed Description section explicitly defines such terms.

What is claimed is:

1. A wearable protective device comprising a gradated composite material, the material comprising:
   a skin-facing cushioning layer;
   a plurality of distinct foam layers, each foam layer having a foam thickness, wherein at least some of the foam layers have differing foam thicknesses, and wherein the foam layers closer to the skin-facing cushioning layer have greater foam thicknesses than the foam layers farther from the skin-facing cushioning layer;
   a plurality of mesh layers, each mesh layer having a mesh porosity, wherein at least some of the mesh layers have differing mesh porosities, and wherein the mesh layers located closer to the skin-facing cushioning layer have higher mesh porosities than the mesh layers located farther from the skin-facing cushioning layer; and
   an outer shell layer harder than the skin-facing cushioning layer, wherein the foam layers and the mesh layers are disposed in an alternating arrangement between the skin-facing cushioning layer and the outer shell layer such that each foam layer is adjacent to at least one mesh layer, and each mesh layer is adjacent to at least one foam layer, wherein the wearable protective device is configured such that, when the wearable protective device is worn by a user, the skin-facing cushioning layer is closer than the outer shell layer to a body of the user.

2. The wearable protective device of claim 1, wherein the foam layers are made of polyurethane foam and the mesh layers are made of carbon fiber mesh.

3. The wearable protective device of claim 1, wherein the skin-facing cushioning layer is made of polyurethane foam and the outer shell layer is made of carbon fiber.

4. The wearable protective device of claim 1, further comprising at least one pressure sensor.

5. The wearable protective device of claim 4, wherein the at least one pressure sensor comprises one or more layers of a piezoresistive material.

6. The wearable protective device of claim 4, wherein the at least one pressure sensor is embedded within one of the plurality of distinct foam layers.

7. The wearable protective device of claim 4, wherein the at least one pressure sensor is configured to detect normal and shear forces applied to the material.

8. A wearable protective device comprising a gradated composite material, the material comprising:
   an inner polyurethane foam layer;
   an outer carbon fiber shell layer harder than the inner polyurethane foam layer; a
   plurality of distinct polyurethane foam layers positioned between the inner polyurethane foam layer and the outer carbon fiber shell layer, each polyurethane foam layer having a foam thickness, the polyurethane foam layers located closer to the inner polyurethane foam layer having greater foam thicknesses than h polyurethane foam layers located farther from the inner polyurethane foam layer;
   a plurality of carbon fiber mesh layers positioned between the inner polyurethane foam layer and the outer carbon fiber shell layer, each carbon fiber mesh layer having a mesh porosity, the carbon fiber mesh layers located closer to the inner polyurethane foam layer having higher mesh porosities than the carbon fiber mesh layers located farther from the inner polyurethane foam layer; and
   one or more piezoresistive material layers configured to detect pressure applied to the gradated composite material,
   wherein the polyurethane foam layers and the carbon fiber mesh layers are positioned in an alternating arrangement such that each polyurethane foam layer is adjacent to at least one carbon fiber mesh layer, and each carbon fiber mesh layer is adjacent to at least one polyurethane foam layer, wherein the wearable protective device is configured such that, when the wearable protective device is worn by a user, the inner polyurethane foam layer is closer than the outer carbon fiber shell layer to a body of the user.

9. An orthopedic device for protecting a patient's foot, the device comprising:
   a foot-receiving portion constructed with a gradated composite material, the gradated composite material comprising:
   an inner cushioning layer;
   a plurality of distinct foam layers, each foam layer having a foam thickness, wherein at least some of the foam layers have differing foam thicknesses; a plurality of mesh layers, each
   mesh layer having a mesh porosity, wherein at least some of the mesh layers have differing mesh porosities; and an outer shell layer,
   wherein the orthopedic device is configured to be worn on the patient's foot; wherein
   when the orthopedic device is worn on the patient's foot, the inner cushioning layer is closer than the outer shell layer to the patient's foot; the foam layers and the mesh layers are positioned in an alternating arrangement such that each foam layer is adjacent to at least one mesh layer, and each mesh layer is adjacent to at least one foam layer; and at least one pressure sensor embedded within the foot-receiving portion and configured to detect pressure on the patient's foot when the device is worn.

10. The device of claim 9, wherein the foam layers are made of polyurethane foam and the mesh layers are made of carbon fiber mesh.

11. The device of claim 9, wherein the plurality of foam layers and the plurality of mesh layers are positioned between the inner cushioning layer and the outer shell layer.

12. The device of claim 11, the foam thicknesses of the plurality of foam layers decrease with increasing distance from the inner cushioning layer.

13. The device of claim 11, wherein the mesh porosities of the plurality of mesh layers decrease with increasing distance from the inner cushioning layer.

14. The device of claim 9, wherein the at least one pressure sensor comprises one or more layers of a piezoresistive material.

15. The device of claim 9, wherein the at least one pressure sensor is configured to detect normal and shear forces on the patient's foot.

16. The device of claim 9, further comprising a transmitter located on or within the foot-receiving portion and configured to transmit pressure data generated by the at least one pressure sensor to an external device.

17. The device of claim 16, wherein the pressure data is transmitted wirelessly.

* * * * *